United States Patent
Agara Venkatesha Rao et al.

(10) Patent No.: US 11,436,737 B2
(45) Date of Patent: Sep. 6, 2022

(54) BRAIN SEGMENTATION USING CLUSTERING AND TEMPLATES

(71) Applicants: Krishna Prasad Agara Venkatesha Rao, Bengaluru (IN); Srinidhi Srinivasa, Bengaluru (IN)

(72) Inventors: Krishna Prasad Agara Venkatesha Rao, Bengaluru (IN); Srinidhi Srinivasa, Bengaluru (IN)

(73) Assignee: Ricoh Company, Ltd., Tokyo (JP)

(*) Notice: Subject to any disclaimer, the term of this patent is extended or adjusted under 35 U.S.C. 154(b) by 362 days.

(21) Appl. No.: 16/734,775

(22) Filed: Jan. 6, 2020

(65) Prior Publication Data

US 2021/0209767 A1    Jul. 8, 2021

(51) Int. Cl.
| | |
|---|---|
| *A61B 5/00* | (2006.01) |
| *G06T 7/174* | (2017.01) |
| *A61B 5/055* | (2006.01) |
| *G06T 11/00* | (2006.01) |
| *G06T 7/11* | (2017.01) |

(52) U.S. Cl.
CPC ........... *G06T 7/174* (2017.01); *A61B 5/0042* (2013.01); *A61B 5/055* (2013.01); *G06T 7/11* (2017.01); *G06T 11/008* (2013.01); *G06T 2207/10088* (2013.01); *G06T 2207/30016* (2013.01)

(58) Field of Classification Search
None
See application file for complete search history.

(56) References Cited

U.S. PATENT DOCUMENTS

| | | | |
|---|---|---|---|
| 2011/0007933 A1* | 1/2011 | Lempitsky | G06T 17/00 382/275 |
| 2016/0019692 A1* | 1/2016 | Jung | A61B 5/7445 382/131 |
| 2017/0147908 A1* | 5/2017 | Chen | G06T 7/0012 |
| 2018/0314691 A1* | 11/2018 | Mori | A61B 5/055 |

* cited by examiner

*Primary Examiner* — Joel F Brutus
(74) *Attorney, Agent, or Firm* — Fenwick & West LLP

(57) ABSTRACT

A cluster-based approach and template-based approach are combined to segment brain matter from a three-dimensional MRI image of voxels. The morphological information captured by the template-based approach may be used to refine the segmentation produced by the cluster-based approach. Conversely, the "similarity" information captured by the cluster-based approach may be used to refine the segmentation produced by the template-based approach.

18 Claims, 8 Drawing Sheets

BRAIN SEGMENTATION USING CLUSTERING AND TEMPLATES

BACKGROUND

1. Technical Field

This disclosure relates generally to brain segmentation of MRI images.

2. Description of Related Art

Segmentation is one step in the analysis of MRI (magnetic resonance imaging) images of brains. A three-dimensional MRI image of a brain typically is a three-dimensional array of voxels, where each voxel has a value (intensity) that represents the response of the matter in that voxel to the MRI imaging process. The segmentation step determines which of the voxels are brain matter and which are not. After the MRI image has been segmented, the voxels that are brain matter may then be further analyzed.

Various approaches have been used to attempt to automate the segmentation step. One approach is based on clustering voxels. In this approach, clusters of "similar" voxels (e.g., similar in intensity) are created, on the assumption that similar voxels represent the same type of matter. However, this is not always a good assumption. For example, different physiological regions may have voxels of similar intensity, and clustering voxels based on intensity would not distinguish between these different regions. Clustering is also sensitive to the starting point chosen for the clustering. It is also affected by noise and intensity variations (e.g., bias field variance). There is also a tendency for clustering approaches to get stuck at local minima rather than finding the best global solution. All of these characteristics are drawbacks to clustering and may lead to erroneous segmentations when using clustering.

Another approach is based on standard templates. In this approach, a standard template of a brain is fit to the MRI image of the actual brain. Voxels that fall within the brain volume of the standard template are labelled as brain matter, and those that are outside the standard brain volume are labelled as not brain matter. The standard template typically is some sort of "average" brain. It may represent the average size and/or shape of a large number of actual brains. However, the template approach does not accurately account for individual variations between brains. For example, individual brains may have unusual features or pathologies. Even for "normal" brains, the location and shape of the fine features of the brain (e.g., sulci and gyri) vary significantly and, as a result, typically are not accounted for by the standard template. In addition, even the "average" brain varies significantly by race and age, for example.

Thus, there is a need for better approaches for brain segmentation of MRI images.

SUMMARY

The present disclosure overcomes the limitations of the prior art by combining the cluster-based approach and the template-based approach. The morphological information captured by the template-based approach may be used to refine the segmentation produced by the cluster-based approach. Conversely, the "similarity" information captured by the cluster-based approach may be used to refine the segmentation produced by the template-based approach.

In one approach, a method for segmenting brain matter from a three-dimensional MRI image of voxels that includes the brain matter includes the following steps. A clustering algorithm is applied to the MRI image to produce a cluster-based segmentation of the MRI image. A template-based algorithm is applied to the MRI image to produce a template-based segmentation of the MRI image. These two segmentations are then iteratively improved using information from the other segmentation. The cluster-based segmentation is improved using information from the template-based segmentation, and the template-based segmentation is improved using information from the cluster-based segmentation. The final segmentation of the MRI image may be based on the improved cluster-based segmentation and/or the improved template-based segmentation.

Other aspects include components, devices, systems, improvements, methods, processes, applications, computer readable mediums, and other technologies related to any of the above.

BRIEF DESCRIPTION OF THE DRAWINGS

Embodiments of the disclosure have other advantages and features which will be more readily apparent from the following detailed description and the appended claims, when taken in conjunction with the examples in the accompanying drawings, in which:

DETAILED DESCRIPTION OF THE PREFERRED EMBODIMENTS

The figures and the following description relate to preferred embodiments by way of illustration only. It should be noted that from the following discussion, alternative embodiments of the structures and methods disclosed herein will be readily recognized as viable alternatives that may be employed without departing from the principles of what is claimed.

FIGS. 1A-1D are flow diagrams for segmenting an MRI image, according to one embodiment. The process begins with a three-dimensional MRI image 110 of the head or a part of the head. Typically, the image 110 is represented by a three-dimensional array of voxels. The nomenclature v or $v_x$ (where the subscript x represents an indexing of the voxels) will be used to represent the voxels. FIG. 2 (prior art) shows one slice of a three-dimensional MRI image of the head. In this example, each voxel $v_x$ has a value (intensity) that represents the response of the matter in that voxel to the MRI imaging process. The intensity values are shown by grayscale in FIG. 2, ranging from black to white. The MRI image 110 includes brain matter but may also include non-brain matter, for example eyes, nasal cavity, skull, muscles, etc. The process of FIG. 1 identifies which of the voxels are brain matter. This process is often referred to as segmentation.

The output of FIG. 1 is a final segmentation 160 of the MRI image 110. In some cases, the final segmentation 160 may be binary, labelling each voxel as either brain matter or not brain matter. In other cases, the final segmentation 160 may be continuous (which here is intended to include multi-value outputs), with each value indicating the probability that each voxel is either brain matter or not brain matter. The final segmentation 160 may also take on non-binary values to indicate that a fraction of the voxel is either brain matter or not brain matter.

Figure 1A:
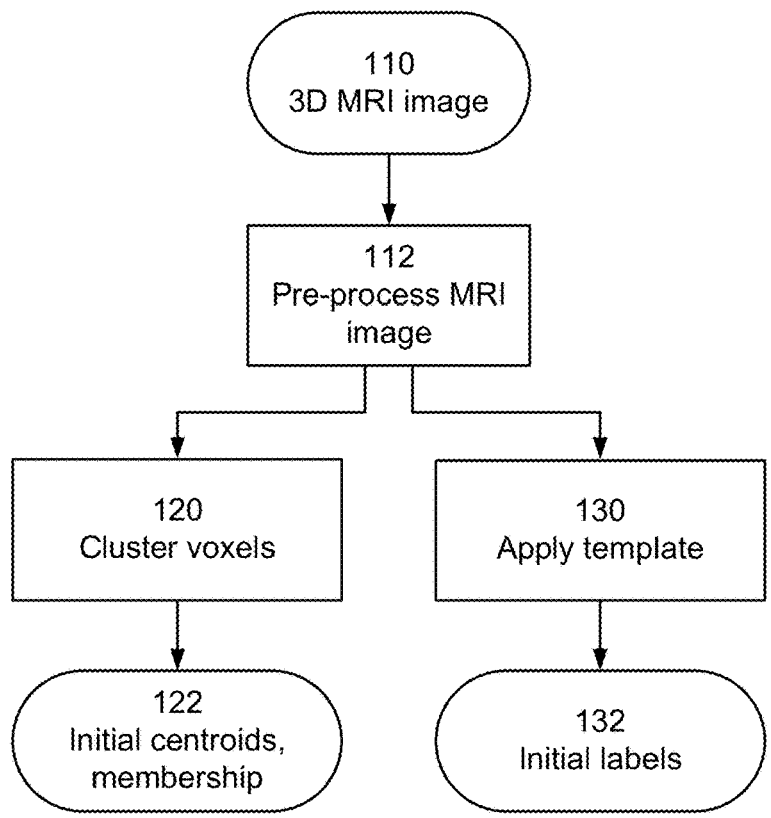
FIGS. 1A-1D are flow diagrams for segmenting an MRI image, according to one embodiment.

As shown in FIG. 1A, the process may begin with pre-processing 112 of the MRI image. Examples of pre-processing include noise filtering and correction of systematic biases. Other examples includes volume resampling (change spacing and resolution), histogram equalization, bias field correction, intensity scaling, standardization and normalization. Pre-processing is optional, and different types of pre-processing may be used. The main portion of FIG. 1 is divided into two flows: one that is cluster-based and one that is template-based. Different pre-processing may be used for each flow.

After pre-processing, an initial cluster-based segmentation 120-122 and an initial template-based segmentation 130-132 are applied to the MRI image, as shown in FIG. 1A. On the left side of FIG. 1A, a clustering algorithm 120 is applied to the MRI image to produce an initial cluster-based segmentation 122 of the image. That is, the voxels of the MRI image are grouped into clusters of "similar" or "close" voxels. In FIG. 1A, the cluster-based segmentation 122 is defined by (a) the centroids for the clusters, and (b) the membership of which voxels belong to which clusters.

Examples of clustering algorithms include k-means clustering, fuzzy c-means clustering, and hierarchical agglomerative clustering. The clustering algorithm itself may be iterative. In one approach, the clustering algorithm starts out with a set of N clusters defined by centroids $C_n$. The voxels $v_x$ are assigned to the cluster with the closest centroid. The centroids are then re-computed based on which voxels are members of that centroid. This iterates until the centroids and their membership converge. In this example, the membership function defines to which cluster each voxel belongs. Let $M_x$ be the membership function for voxel $v_x$. Then $M_x$=(cluster to which voxel $v_x$ belongs). The cluster may be identified by a cluster number, the cluster's centroid, or some other identifier. In an alternative approach, the membership function is more probabilistic. For example, membership function $M_{x,n}$=(probability that voxel $v_x$ belongs to cluster n). Other membership functions may also be used.

Clustering may be based on various quantities, such as intensities of the voxels or physical locations of the voxels. If the clustering is based on intensity, the centroids $C_n$ are defined as different intensity values, and the voxels are assigned to clusters based on how close their intensity values are to each of the centroids. Clustering may also be based on multiple quantities, such as intensity and physical location. In that case, each centroid $C_n$ is defined by an intensity and a physical coordinate, and the voxels are assigned based on similarity of intensity and physical proximity.

On the right side of FIG. 1A, a template-based algorithm 130 is applied to the MRI image to produce a template-based segmentation 132 of the MRI image. In template-based approaches, a known template of the brain is applied to the MRI image. This template may represent an "average" or "typical" brain. The template typically defines a three-dimensional brain surface. Voxels that are located in an interior volume defined by the surface are classified as brain matter and voxels outside the brain surface are not.

In FIG. 1A, the template-based segmentation 132 is defined by labels that identify whether each voxel is or is not brain matter. Let $L_x$ be the label function for voxel $v_x$. Then $L_x$=(whether voxel $v_x$ is brain matter). The label function may be binary, meaning that every voxel is classified as either brain matter or not brain matter. Alternatively, the label function may be continuous. For example, label function $L_x$=(probability that voxel $v_x$ is brain matter) or $L_x$= (fraction of voxel $v_x$ that is brain matter) or $L_x$=(expected fraction of voxel $v_x$ that is brain matter). Other label functions may also be used.

Figure 2:
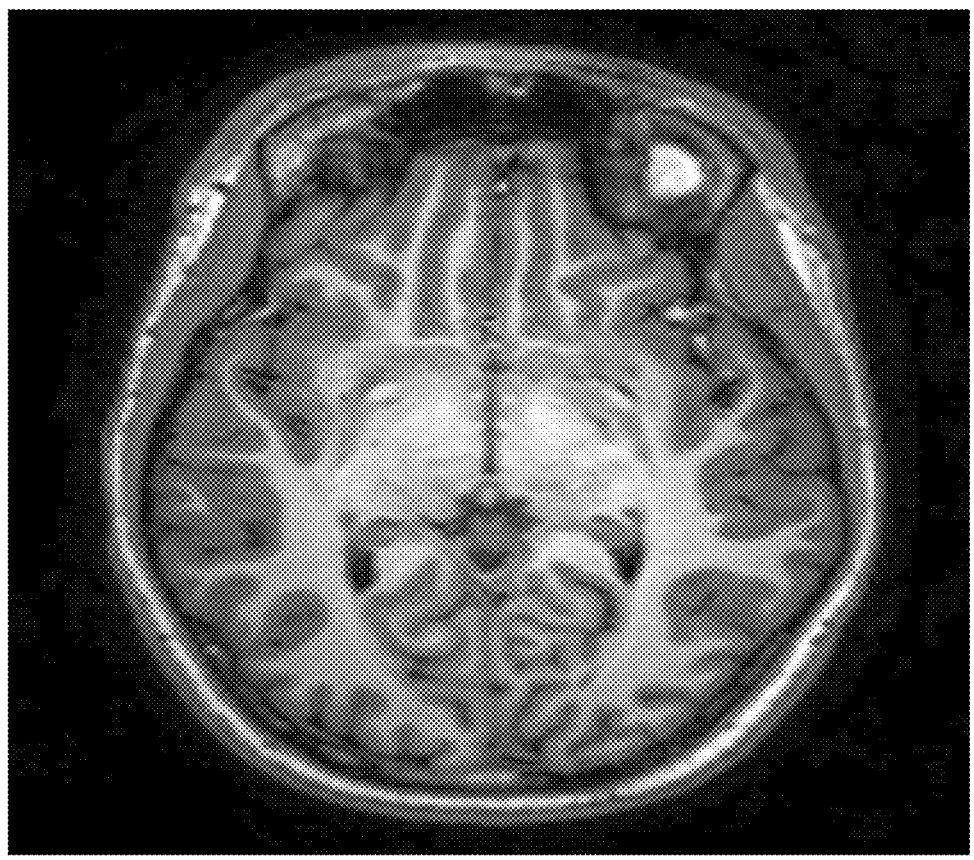
FIG. 2 (prior art) is one slice of a three-dimensional MRI image.
Figure 3A:
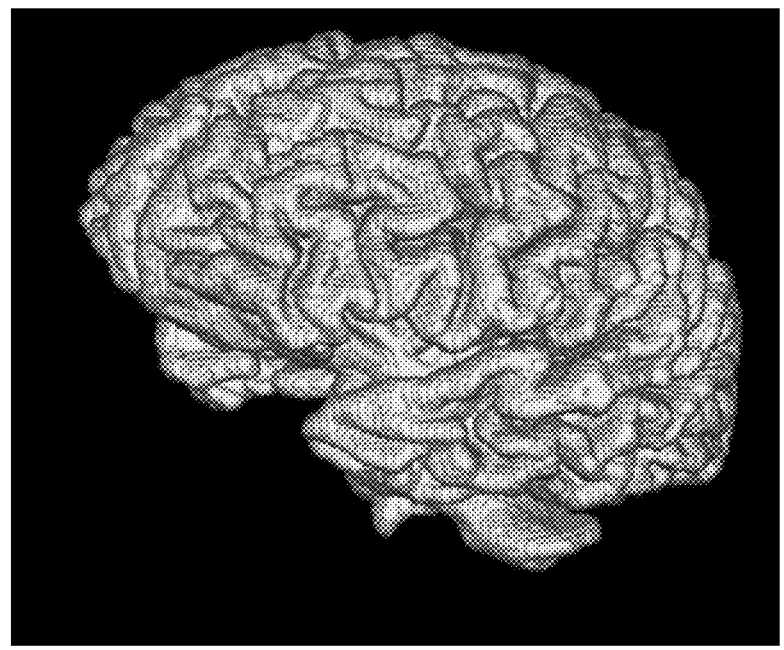
FIGS. 3A and 3B show an actual brain and a cluster-based segmentation of the brain, respectively.
Figure 3B:
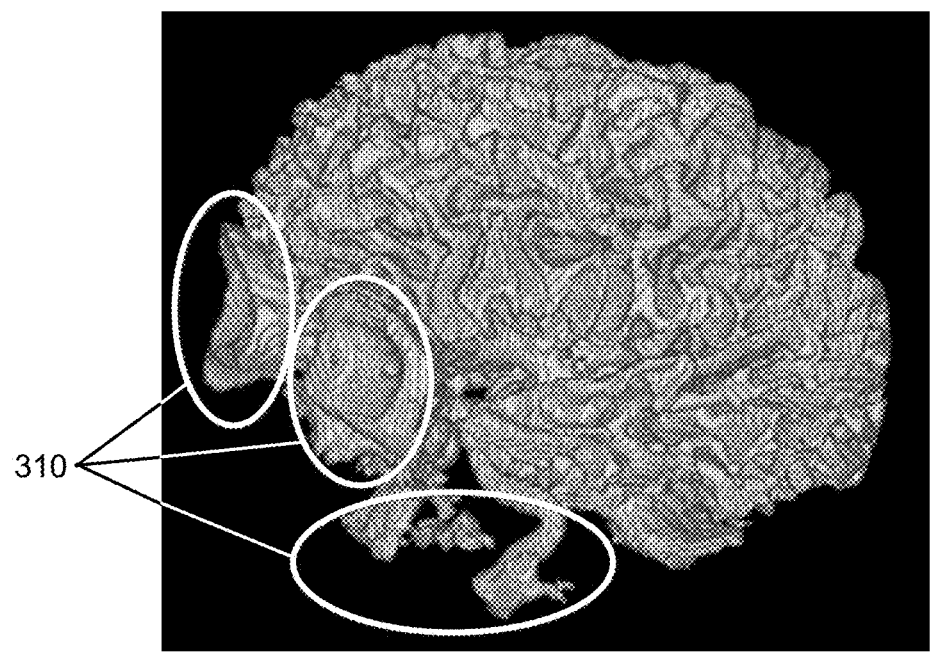
Figure 4A:
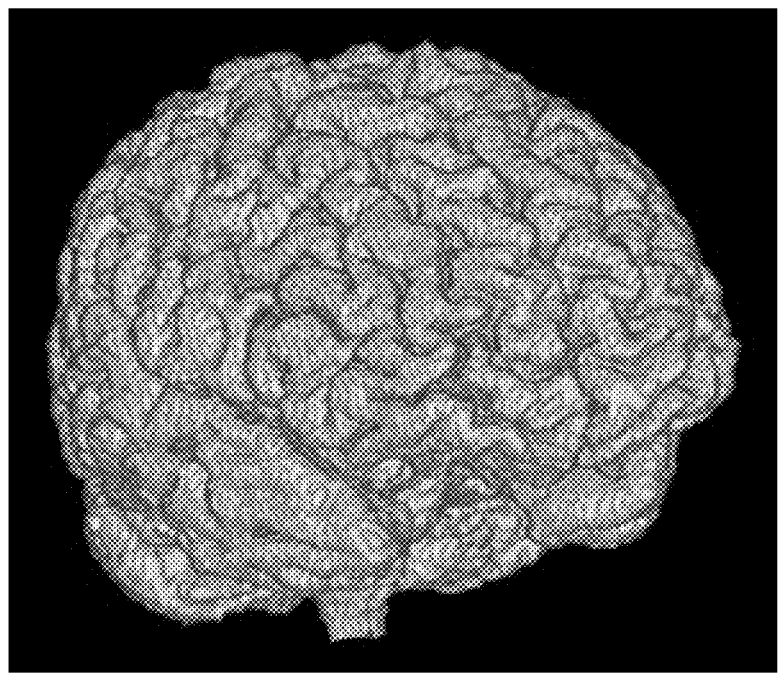
FIGS. 4A and 4B show an actual brain and a template-based segmentation of the brain, respectively.
Figure 4B:
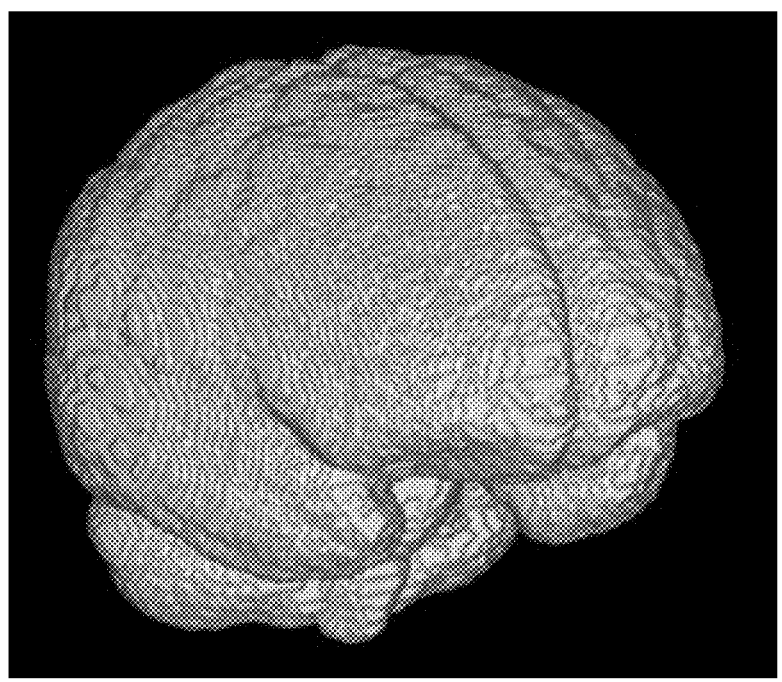

However, because of the drawbacks described above, the initial cluster-based segmentation 122 and the initial template-based segmentation 132 typically are not very accurate. FIGS. 3A and 3B show an actual brain and a cluster-based segmentation of the brain, respectively. In the cluster-based segmentation of FIG. 3B, the circled matter 310 (e.g., eyes) are erroneously included with the brain clusters because they have similar intensities as the brain matter. This can be seen in FIG. 2. The intensities present in the brain are not unique to the brain and may be present also in other structures. If intensity-based clustering is used, the cluster-based segmentation will not distinguish between these brain and non-brain structures of similar intensity. FIGS. 4A and 4B show an actual brain and a template-based segmentation of the brain, respectively. In this example, the template has a relatively smooth brain surface, so the template-based segmentation of FIG. 4B does not accurately represent the fine sulci and gyri shown in FIG. 4A.

Figure 1B:
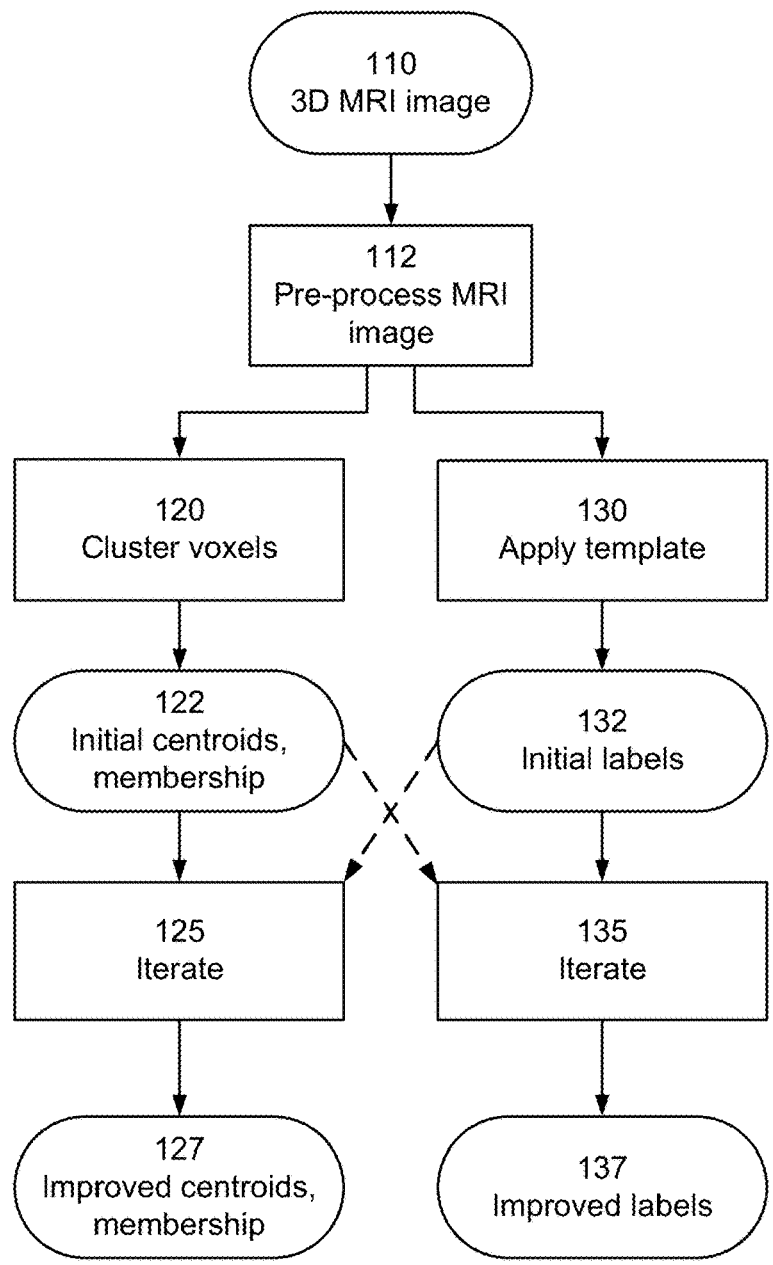

In FIG. 1B, the initial cluster-based segmentation 122 is improved 125 using information from the template-based segmentation 132. Similarly, the initial template-based segmentation 132 is improved 135 using information from the cluster-based segmentation 122. For example, in FIG. 3B, the purely cluster-based approach groups eye matter with brain matter due to their similar intensities. However, the template-based approach recognizes that the eye matter is not part of the brain and this morphological information may be used to improve the cluster-based segmentation. Conversely, in FIG. 4B, the purely template-based approach produces a smooth brain without the individual sulci and gyri. However, the cluster-based approach distinguishes these features because matter inside and outside the brain will belong to different clusters and this information may be used to improve the template-based segmentation.

Figure 1C:
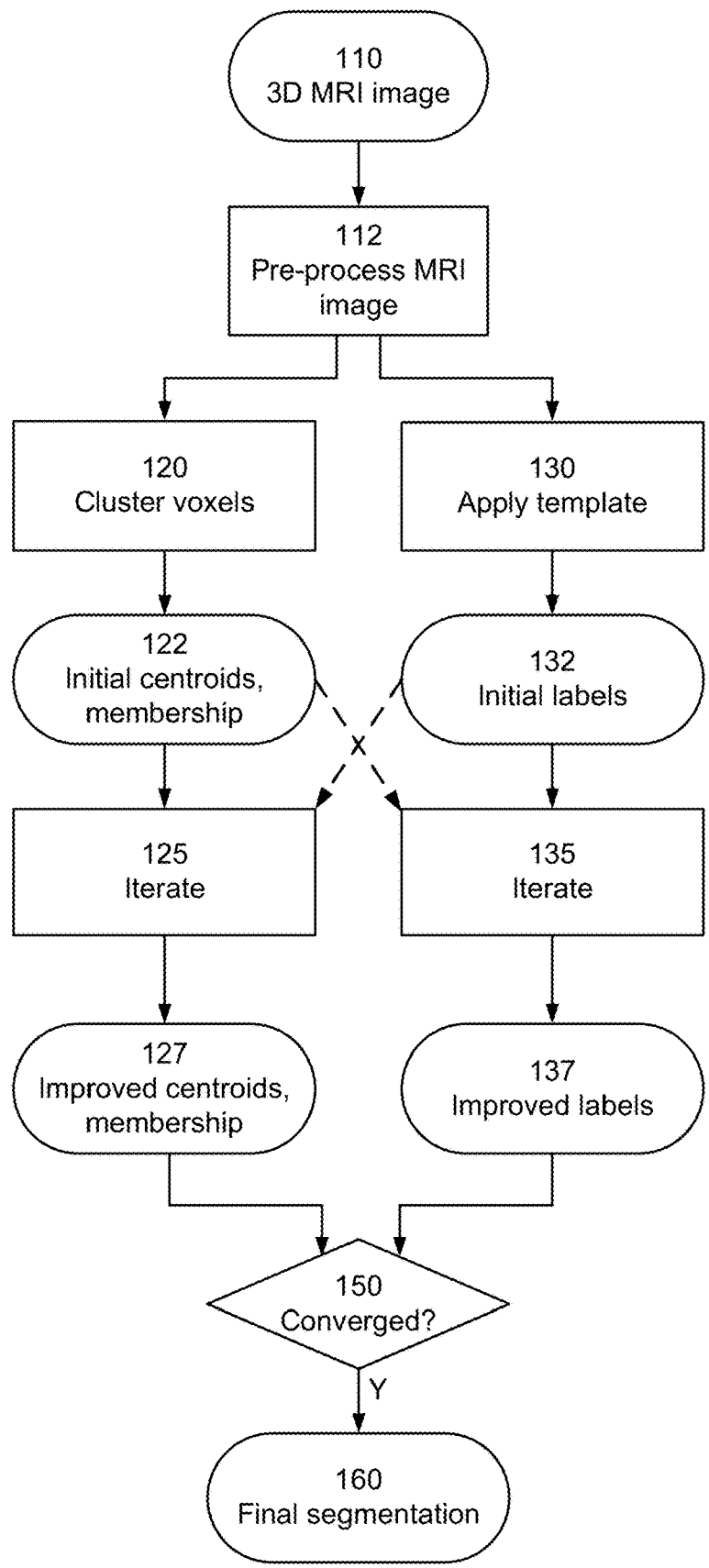
Figure 1D:
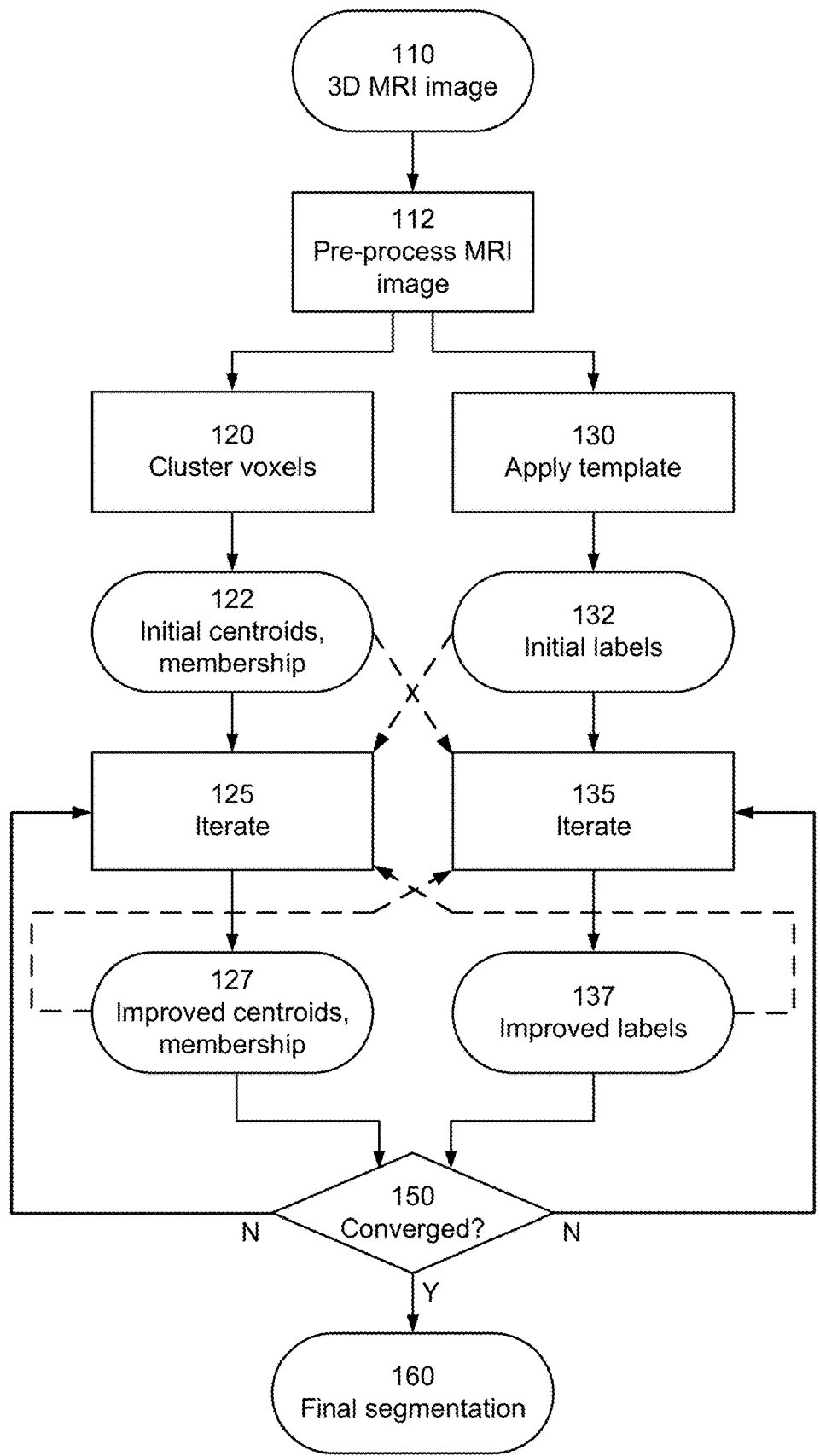

In FIG. 1C, if the segmentations 127, 173 are sufficiently improved 150, then the final segmentation 160 may be produced. Otherwise, additional iterations 125, 135 are run to further improve the segmentations, as shown in FIG. 1D. The cluster-based segmentation 127 is further improved, using information from the updated template-based segmentation 137. Similarly, the template-based segmentation 137 is further improved, using information from the updated cluster-based segmentation 127. Note that as these iterations proceed, the "cluster-based" segmentation 127 will no longer be based purely on clustering and the "template-based" segmentation 137 will no longer be based purely on templates. However, these names will be retained for clarity.

In addition, because the initial segmentations 122, 132 are further improved, the initial clustering 120 and templates 130 need not have the same accuracy compared to if they were used to produce final segmentations. For example, the template 130 may be coarser compared to an approach that relies only on templates. They may not have sufficient resolution to capture all physiological structures, as would be desirable if the template were used to produce the final segmentation. Analogously, the number of clusters may be reduced compared to an approach where the clustering is used to produce the final segmentation. Coarser templates and fewer clusters have an advantage of faster run-times.

The final segmentation may be based on either the cluster-based segmentation 127, the template-based segmentation 137 or both. Once the brain matter has been identified, the resulting images may be used for different purposes. For examples, doctors may use the brain image as a a guide before proceeding with brain surgery. Brain images may also be used in encephalography (magnetoencephalography and electroencephalograhy) to map which region of the brain is the cause of certain neurological disorders.

In one approach, the iterations 125, 135 are based on an objective function that is a function of both the cluster-based segmentation 127 and the template-based segmentation 137. The objective function is improved by alternately (a) optimizing 125 the cluster-based segmentation while holding the template-based segmentation constant, and (b) optimizing 135 the template-based segmentation while holding the cluster-based segmentation constant.

For example, consider an objective function $$J = \Sigma_k(\alpha_{cb} \mathbb{C}_{cb}^k + \alpha_{tb} \mathbb{C}_{tb}^k) \quad (1)$$

where the summation is over different scales k, $\mathbb{C}_{cb}^k$ is the clique potential $\mathbb{C}$ of the cluster-based segmentation 137 (the subscript cb stands for cluster-based) at scale k, and $\mathbb{C}_{tb}^k$ is the clique potential $\mathbb{C}$ of the template-based segmentation 127 (the subscript tb stands for template-based) at scale k. The two terms $\mathbb{C}_{cb}^k$ and $\mathbb{C}_{tb}^k$ are weighted by $\alpha_{cb}$ and $\alpha_{tb}$, respectively.

The kernel within the parenthesis is a function of both the cluster-based segmentation and the template-based segmentation. In the formulation described above, it is a function of the centroids $C_n$, the membership function $M_x$ and the label function $L_x$. The generic kernel is evaluated at different scales and summed to produce the objective function J. The number of scales and their spacing may be empirically determined for given data set. Weighted multiscale and uniform multiscale are two examples. One advantage of using a multiscale objective function is its efficacy in solving problems at multiple scales, since different features and physiological regions become prominent at different scales. Multiscale filtering also results in some amount of regularization and noise removal.

Continuing the above example, assume that the membership function $M_x$ is binary so that each voxel x is assigned to a specific cluster with centroid $C_n$. Also assume that the label function $L_x$ is binary so that each voxel x is labeled as either brain matter or not brain matter. The clique potential $\mathbb{C}$ is a measure of disorder and is defined as:

$$\mathbb{C} = \sum_x \sum_{y \in N(x)} \begin{cases} (C_x - v_y)^2 : \text{if } L_x = L_y \\ 0 : \text{if } L_x \neq L_y \end{cases} \quad (2)$$

where $\Sigma_x$ is a summation over each voxel x in the volume of interest; $\Sigma_{y \in N(x)}$ is a summation over all voxels y that fall within a neighborhood N(x) of voxel x; $C_x$ is the centroid value of the cluster to which voxel x belongs; $v_y$ is the value of voxel y; and $L_x$ and $L_y$ are the labels for voxels x and y.

Note that the clique potential $\mathbb{C}$ is a function both of the cluster-based segmentation (through the use of $C_x$) and of the template-based segmentation (through the use of $L_x$).

The clique potential $\mathbb{C}$ may be evaluated at different scales and for different brain segmentations. In Eqn. 1, $\mathbb{C}_{cb}^k$ is the clique potential $\mathbb{C}$ evaluated at scale k where the summation is over voxels defined by the cluster-based segmentation, and $\mathbb{C}_{tb}^k$ is the clique potential $\mathbb{C}$ evaluated at scale k where the summation is over voxels defined by the template-based segmentation.

Referring to FIG. 1 and using the objective function J, the cluster-based segmentation is improved 125 by optimizing J with respect to the centroids $C_n$ and membership function $M_x$, while holding the label function $L_x$ from the template-based segmentation constant. Gradient-based methods may be used. The objective function J in Eqn. 1 has two terms: one for the cluster-based segmentation and one for the template-based segmentation. Thus, gradient-based methods may also be implemented using these two terms. Let $J_{cb} = \Sigma_k(\mathbb{C}_{cb}^k)$ and $J_{tb} = \Sigma_k(\mathbb{C}_{tb}^k)$. The gradients for each of these terms may be expressed as $$\sum_n \left[ \frac{\partial J_{cb}}{\partial C_n} \right] \text{ and } \sum_n \left[ \frac{\partial J_{tb}}{\partial C_n} \right],$$

respectively, where the summation is over all of the centroids. Gradient descent, stochastic gradient descent, batch and mini batch gradient descent are different optimization methods that may be used.

Referring to iteration 135 of FIG. 1, refinement of the template-based segmentation involves flipping labels $L_x$ to identify the label configuration with best objective function J. In one approach, this may be treated as a constrained optimization problem of figuring out the optimal set of labels in a multi-resolution neighborhood. Let the set of all labels be represented as L. In a selected neighborhood of a given scale (resolution), we have a label-oriented neighborhood representation: lab={$lab_v$, $v \in V$}, where V is a three-dimensional volume neighborhood and v is each voxel. For a neighborhood of size j×k×l, there are $|L|^{jkl}$ possible labels. The goal of template segmentation refinement 135 is to arrive at optimal low cost label configuration in the chosen neighborhood, at a given scale or resolution: argmax P(lab-|Centroid Intensity), for all voxels, where 'P' is posterior probability.

Figure 5:
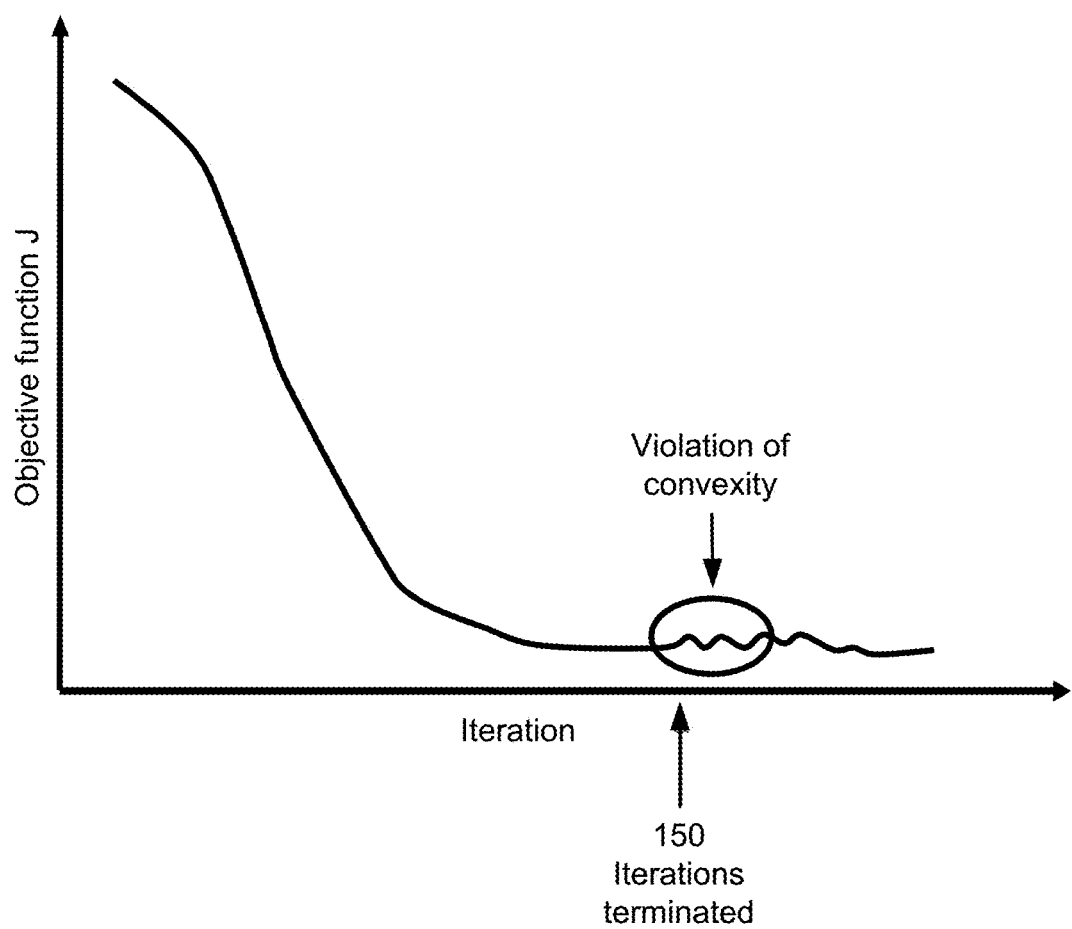
FIG. 5 is a diagram showing the termination of iterations upon violation of the convexity principle.

As iterations are run, the objective function J improves. The derivative $$\left( \frac{\partial J}{\partial \text{Iteration}} \right)$$

may be calculated. Lower and higher order derivatives of the cost with respect to iteration may also be computed. In one approach, when the convexity principle is violated, as shown in FIG. 5, the iterations are ended 150 and the final segmentation 160 is produced.

Although the detailed description contains many specifics, these should not be construed as limiting the scope of the invention but merely as illustrating different examples. It should be appreciated that the scope of the disclosure includes other embodiments not discussed in detail above. Various other modifications, changes and variations which will be apparent to those skilled in the art may be made in the arrangement, operation and details of the method and apparatus disclosed herein without departing from the spirit and scope as defined in the appended claims. Therefore, the scope of the invention should be determined by the appended claims and their legal equivalents.

Alternate embodiments are implemented in computer hardware, firmware, software, and/or combinations thereof. Implementations can be implemented in a computer program product tangibly embodied in a computer-readable storage device for execution by a programmable processor; and method steps can be performed by a programmable processor executing a program of instructions to perform functions by operating on input data and generating output. Embodiments can be implemented advantageously in one or more computer programs that are executable on a programmable computer system including at least one programmable processor coupled to receive data and instructions from, and to transmit data and instructions to, a data storage system, at least one input device, and at least one output device. Each computer program can be implemented in a high-level procedural or object-oriented programming language, or in assembly or machine language if desired; and in any case, the language can be a compiled or interpreted language. Suitable processors include, by way of example, both general and special purpose microprocessors. Generally, a processor will receive instructions and data from a read-only memory and/or a random access memory. Generally, a computer will include one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM disks. Any of the foregoing can be supplemented by, or incorporated in, ASICs (application-specific integrated circuits), FPGAs and other forms of hardware.

What is claimed is:

1. A method for segmenting brain matter from a three-dimensional MRI image of voxels that includes the brain matter, the method implemented on a computer system executing instructions comprising:
    applying a clustering algorithm to an MRI image to produce a cluster-based segmentation of the MRI image, wherein the cluster-based segmentation is defined by (a) centroids for a set of clusters, and (b) a membership function indicative of probabilities of voxels belonging to clusters;
    applying a template-based algorithm to the MRI image to produce a template-based segmentation of the MRI image, wherein the template-based segmentation is defined by a label function indicative of probabilities of voxels being located in an interior space of a template;
    iteratively improving the cluster-based segmentation using information from the template-based segmentation, comprising improving an objective function by optimizing the centroids and the membership function, while holding the label function constant, wherein the objective function is a function of the centroids, of the membership function and of the label function;
    iteratively improving the template-based segmentation using information from the cluster-based segmentation, comprising improving the same objective function by optimizing the label function while holding the centroids and the membership function constant; and
    producing a final segmentation of the MRI image based on the improved cluster-based segmentation and/or the improved template-based segmentation.

2. The method of claim 1 wherein the objective function comprises a sum of a generic kernel evaluated at different scales, and the generic kernel is a function of the centroids, of the membership function and of the label function.

3. The method of claim 2 wherein the generic kernel is a measure of clique potential.

4. The method of claim 1 wherein the objective function comprises a term based on the template-based segmentation and a different term based on the cluster-based segmentation.

5. The method of claim 1 wherein iteratively improving the cluster-based segmentation and the template-based segmentation end when the objective function violates a convexity criterion.

6. The method of claim 1 wherein the clustering algorithm clusters the voxels based at least in part on intensities of the voxels.

7. The method of claim 1 wherein the clustering algorithm clusters the voxels based at least in part on physical locations of the voxels.

8. The method of claim 1 wherein iteratively improving the cluster-based segmentation uses morphological information from the template-based segmentation.

9. The method of claim 1 wherein applying the template-based algorithm to the MRI image comprises applying a first template to segment the voxels of the MRI image, and the first template is too coarse to distinguish individual sulci and gyri.

10. The method of claim 1 wherein the label function is a binary function.

11. The method of claim 1 wherein the label function is a continuous function.

12. The method of claim 1 wherein the final segmentation of the MRI image is based on either the cluster-based segmentation or the template-based segmentation but not both.

13. The method of claim 1 wherein the final segmentation of the MRI image is binary.

14. The method of claim 1 wherein the final segmentation of the MRI image is continuous.

15. The method of claim 1 further comprising:
    applying noise removal to the MRI image before applying the clustering algorithm and before applying the template-based algorithm.

16. The method of claim 1 further comprising:
    using the final segmented MRI image in encephalography to identify which region of the brain is a cause of a neurological disorder.

17. A non-transitory computer-readable storage medium storing executable computer program instructions for segmenting brain matter from a three-dimensional MRI image of voxels that includes the brain matter, the instructions executable by a computer system and causing the computer system to perform a method comprising:
    applying a clustering algorithm to the MRI image to produce a cluster-based segmentation of the MRI image, wherein the cluster-based segmentation is defined by (a) centroids for a set of clusters, and (b) a membership function indicative of probabilities of voxels belonging to clusters;
    applying a template-based algorithm to the MRI image to produce a template-based segmentation of the MRI image, wherein the template-based segmentation is defined by a label function indicative of probabilities of voxels being located in an interior space of a template;

iteratively improving the cluster-based segmentation using information from the template-based segmentation, comprising improving an objective function by optimizing the centroids and the membership function, while holding the label function constant, wherein the objective function is a function of the centroids, of the membership function and of the label function;

iteratively improving the template-based segmentation using information from the cluster-based segmentation, comprising improving the same objective function by optimizing the label function while holding the centroids and the membership function constant; and producing a final segmentation of the MRI image based on the improved cluster-based segmentation and/or the improved template-based segmentation.

18. A method for segmenting brain matter from a three-dimensional MRI image of voxels that includes the brain matter, the method implemented on a computer system executing instructions comprising:

applying a clustering algorithm to the MRI image to produce a cluster-based segmentation of the MRI image;

applying a template-based algorithm to the MRI image to produce a template-based segmentation of the MRI image;

iteratively improving the cluster-based segmentation using information from the template-based segmentation;

iteratively improving the template-based segmentation using information from the cluster-based segmentation;

producing a final segmentation of the MRI image based on the improved cluster-based segmentation and/or the improved template-based segmentation;

wherein iteratively improving the cluster-based segmentation and iteratively improving the template-based segmentation comprise iteratively improving an objective function that is a function of both the cluster-based segmentation and the template-based segmentation, by alternately (a) improving the objective function by optimizing the cluster-based segmentation while holding the template-based segmentation constant, and (b) improving the objective function by optimizing the template-based segmentation while holding the cluster-based segmentation constant.

* * * * *